United States Patent
Kerdok et al.

(10) Patent No.: US 11,944,399 B2
(45) Date of Patent: Apr. 2, 2024

(54) SYSTEM AND METHOD FOR ARTICULATED ARM STABILIZATION

(71) Applicant: INTUITIVE SURGICAL OPERATIONS, INC., Sunnyvale, CA (US)

(72) Inventors: Amy E. Kerdok, San Jose, CA (US); Margaret M. Nixon, San Jose, CA (US); Douglas S. Langley, Millford, CT (US); Wesley Swanson, Cupertino, CA (US); Mahdi Azizian, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/152,914

(22) Filed: Jan. 11, 2023

(65) Prior Publication Data
US 2023/0149104 A1   May 18, 2023

Related U.S. Application Data

(60) Continuation of application No. 16/503,367, filed on Jul. 3, 2019, now Pat. No. 11,583,351, which is a (Continued)

(51) Int. Cl.
*A61B 34/35*   (2016.01)
*A61B 34/00*   (2016.01)
(Continued)

(52) U.S. Cl.
CPC .............. *A61B 34/35* (2016.02); *A61B 34/30* (2016.02); *A61B 34/75* (2016.02); *A61B 34/76* (2016.02); *A61B 90/57* (2016.02)

(58) Field of Classification Search
CPC ......... A61B 34/35; A61B 34/30; A61B 34/75; A61B 34/76; A61B 90/57
(Continued)

(56) References Cited

U.S. PATENT DOCUMENTS

| 1,613,683 | A | 1/1927 | Utz |
| 2,079,227 | A | 5/1937 | Raymond et al. |

(Continued)

FOREIGN PATENT DOCUMENTS

JP   2006336732 A   12/2006

OTHER PUBLICATIONS

International Search Report and Written Opinion for Application No. PCT/US2015/058237, dated Feb. 1, 2016, 8 pages.
(Continued)

*Primary Examiner* — Jaime Figueroa
(74) *Attorney, Agent, or Firm* — Haynes & Boone, LLP.

(57) ABSTRACT

A computer-assisted medical device includes a first articulated arm, a second articulated arm, an arm stabilizer, and a control system. The arm stabilizer includes first and second clamps and one or more sensors. The first and second clamps are configured to couple the arm stabilizer to the first and second articulated arms. At least one of a distance or a relative orientation between the first and second clamps is adjustable and the one or more sensors are configured to determine the distance or relative orientation. The control system is configured to implement a following mode in which the control system drives movement of the second articulated arm in response to movements of the first articulated arm and the arm stabilizer.

20 Claims, 4 Drawing Sheets

Related U.S. Application Data division of application No. 15/522,568, filed as application No. PCT/US2015/058237 on Oct. 30, 2015, now Pat. No. 10,376,324.

(60) Provisional application No. 62/072,623, filed on Oct. 30, 2014.

(51) Int. Cl.
*A61B 34/30* (2016.01)
*A61B 90/57* (2016.01)

(58) Field of Classification Search
USPC .................................. 700/245–264; 606/130
See application file for complete search history.

(56) References Cited

U.S. PATENT DOCUMENTS

| | | | |
|---|---|---|---|
| 2,271,935 | A | 2/1942 | Buchanan et al. |
| 5,098,048 | A | 3/1992 | Chen |
| 5,968,060 | A | 10/1999 | Kellogg |
| 6,102,850 | A | 8/2000 | Wang et al. |
| 6,152,406 | A | 11/2000 | Denndou |
| 6,364,888 | B1 | 4/2002 | Niemeyer et al. |
| 6,587,750 | B2 | 7/2003 | Gerbi et al. |
| 6,660,017 | B2 | 12/2003 | Beaupre |
| 7,335,997 | B2 | 2/2008 | Wiener |
| 8,136,713 | B2 | 3/2012 | Hathaway et al. |
| 8,332,072 | B1 | 12/2012 | Schaible et al. |
| 8,512,365 | B2 | 8/2013 | Wiener et al. |
| 8,770,537 | B2 | 7/2014 | Go |
| 8,911,460 | B2 | 12/2014 | Neurohr et al. |
| 9,883,884 | B2 | 2/2018 | Neurohr et al. |
| 10,028,765 | B2 | 7/2018 | Hibner et al. |
| 10,368,878 | B2 | 8/2019 | Lavallee et al. |
| 10,376,324 | B2 | 8/2019 | Kerdok et al. |
| 10,383,674 | B2 * | 8/2019 | Sexson .............. A61B 17/1626 |
| 10,820,951 | B2 | 11/2020 | Soundararajan et al. |
| 10,898,219 | B2 | 1/2021 | Shelton, IV et al. |
| 10,987,123 | B2 | 4/2021 | Weir et al. |
| 11,583,351 | B2 | 2/2023 | Kerdok et al. |
| 2004/0217236 | A1 | 11/2004 | Shibuya |
| 2005/0098697 | A1 | 5/2005 | Collins |
| 2007/0142968 | A1 | 6/2007 | Prisco et al. |
| 2007/0283970 | A1 | 12/2007 | Mohr et al. |
| 2007/0284485 | A1 | 12/2007 | Kato |
| 2008/0163921 | A1 | 7/2008 | Leong et al. |
| 2009/0062813 | A1 * | 3/2009 | Prisco .................... A61B 34/37 606/130 |
| 2009/0143796 | A1 | 6/2009 | Stulen et al. |
| 2010/0170362 | A1 * | 7/2010 | Bennett .................. A61B 34/30 901/21 |
| 2010/0249817 | A1 | 9/2010 | Mark |
| 2011/0015627 | A1 | 1/2011 | DiNardo et al. |
| 2011/0046338 | A1 | 2/2011 | Chang |
| 2011/0095158 | A1 | 4/2011 | Laker |
| 2011/0130780 | A1 | 6/2011 | Slipszenko et al. |
| 2012/0073764 | A1 * | 3/2012 | Lawson ................ G01M 1/326 157/1.1 |
| 2013/0172858 | A1 | 7/2013 | Doyle |
| 2013/0205558 | A1 | 8/2013 | Sporer et al. |
| 2013/0244820 | A1 | 9/2013 | Solomon et al. |
| 2014/0005705 | A1 | 1/2014 | Weir et al. |
| 2015/0054753 | A1 * | 2/2015 | Morgan ................. A61B 34/76 345/173 |
| 2015/0231942 | A1 | 8/2015 | Trangbaek et al. |
| 2016/0022374 | A1 | 1/2016 | Haider et al. |
| 2016/0030118 | A1 | 2/2016 | Devengenzo et al. |
| 2016/0081754 | A1 | 3/2016 | Kostrzewski et al. |
| 2016/0288325 | A1 | 10/2016 | Naderer et al. |
| 2017/0079730 | A1 | 3/2017 | Azizian et al. |
| 2017/0348037 | A1 * | 12/2017 | Sexson .................. A61B 90/03 |
| 2018/0014846 | A1 | 1/2018 | Rhee et al. |
| 2019/0321116 | A1 | 10/2019 | Kerdok et al. |
| 2019/0327394 | A1 | 10/2019 | Ramirez Luna et al. |
| 2019/0366556 | A1 * | 12/2019 | Wang .................. B25J 15/0293 |
| 2020/0405416 | A1 | 12/2020 | Shelton, IV et al. |
| 2021/0007815 | A1 | 1/2021 | Soundararajan et al. |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEM AND METHOD FOR ARTICULATED ARM STABILIZATION

RELATED APPLICATIONS

This patent application is a continuation of U.S. patent application Ser. No. 16/503,367, filed on Jul. 3, 2019, which is a divisional of U.S. patent application Ser. No. 15/522,568, filed Apr. 27, 2017, which is a U.S. National Stage patent application of International Patent Application No. PCT/US2015/058237 filed on Oct. 30, 2015, the benefit of which is claimed, and further claims priority to and the benefit of the filing date of U.S. Provisional Patent Application 62/072,623, entitled "SYSTEM AND METHODS FOR ARTICULATED ARM STABILIZATION," filed Oct. 30, 2014, each of which is incorporated by reference herein in its entirety.

TECHNICAL FIELD

The present disclosure relates generally to operation of devices with articulated arms and more particularly to stabilization of articulated arms.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms, end effectors and/or imaging devices. When the articulated arms and/or the end effectors include redundant degrees of freedom (i.e., more than the six degrees of freedom typically associated with Cartesian x, y, and z positioning and roll, pitch, and yaw orientations), the articulated arms and/or the end effectors may provide extensive flexibility in adjusting to changes in patient size, position, and/or orientation as the articulated arms and/or the end effectors are used to support medical procedures. This is possible because the redundant degrees of freedom allow the articulated arms and/or the end effectors to be positioned so as to avoid collisions among themselves, the patient, and/or other devices and personnel in an operating room and/or interventional suite.

Many medical procedures call for high precision in the positioning, orientation, and/or stability of the medical tools and/or devices used to perform the procedures. Computer-assisted medical devices with articulated arms have been used for years to perform high precision medical procedures, with the vast majority of these procedures being performed in the abdomino-pelvic cavities of the patient. There are many reasons for this including the large variety of possible abdomino-pelvic procedures and the characteristics of the anatomy of the abdomino-pelvic region, just to name a few. In some cases, a contributing factor may also be related to the realistic limitations of the computer-assisted medical devices and their articulated arms. In some examples, an articulated arm may have a practical upper limit on the amount of force and/or torque that the articulated arm may exert on a tool tip or end effector located at the distal end of the articulated arm due to such factors as the length of the articulated arm, the mass of the tool tip and/or end effector, the size of the actuators of the articulated arm, and/or the like. In some examples, the electro-mechanical systems of the articulated arm, the end effector, and/or the tool tip may also be subject to small oscillations and/or vibrations that may result in less than desirable vibrations in the tool top and/or the end effector. In some examples, the oscillations or vibrations may vary based on the mass of the end effector, tool tip, and/or imaging device located at the cantilevered end of the articulated arm and/or the position of the articulated arm.

In many circumstances, laparoscopic procedures with manually operated laparoscopic instruments may be subject to similar limitations. In many cases, a patient may introduce additional conditions that a stand-alone teleoperated system may not have. In some examples, physiological motions associated with respiration, heart beats, and/or the like may introduce motion to the end effector, tool tip, and/or imaging device that may be less than desirable as well.

During some procedures, the operator of the computer-assisted medical device may be able to suitably compensate for the oscillations and/or vibrations as long as the amplitude and/or frequency are not too large. In some examples, compensating for the oscillations and/or vibrations may significantly increase the fatigue of an operator.

In general, however, the limitations of the computer-assisted medical device and its articulated arms may be reduced and/or substantially eliminated during abdomino-pelvic procedures because of how the tool tips, end effectors, and/or imaging devices (such as an endoscope) pass through the body wall of the patient. During many procedures, the tool tips, end effectors, and/or imaging devices are passed through a hollow cannula that is inserted through an incision in the patient. The skin and the abdominal wall of the patient act on the cannula to both stabilize the tool tips, end effectors, and/or imaging devices and to absorb the vibrations. For minimally invasive medical procedures where there is a non-compliant body wall supporting the cannula (e.g., through the ribs in cardiac and thoracic procedures), a non-circumferential retainer on the cannula (e.g., procedures where multiple cannulas go through the same larger incision, such as transaxial thyroidectomy), a thin or frail body wall (e.g., pediatric or elderly patients), or no constraint/body wall at all (e.g., transoral, transanal, transvaginal, eye surgery, or extremity reconstructive procedures) the body wall alone may not be able to provide sufficient stabilization and/or vibration absorption to support many medical procedures where precision is important.

Stabilization and/or vibration reduction may be improved through the use of tool jigs that are attached to the patient or surgical table, mounted on table-side stands, mounted to ceiling fixtures, and/or the like. Many of these tool jigs, however, may have limitations in their degrees of freedom, size, and/or the like that significantly limit their ability to be used with patients of different sizes, different positions within the anatomy of the patients, interacting with different ancillary equipment, and/or with different procedures. These tool jigs may also have a limited ability to adapt to changes in patient position and/or orientation during a procedure. Additional flexibility may be obtained by using different tool jigs for different procedures, but the number of possible patients, positions, and/or procedures may involve an unacceptably large number of tool jigs.

Accordingly, it would be advantageous to develop systems and methods for vibration reduction and stabilization of the articulated arms, end effectors, and/or tool tips of computer assisted medical devices.

SUMMARY

Consistent with some embodiments, an arm stabilizer for use with articulated arms of a computer-assisted medical device includes a spine, a first vibration absorbing mount attached to the spine, a second vibration absorbing mount attached to the spine, a first clamp attached to the first vibration absorbing mount, and a second clamp attached to the second vibration absorbing mount. The first clamp is adapted to hold a first attachment point of a first articulated arm without slipping. The second clamp is adapted to hold a second attachment point of a second articulated arm without slipping.

Consistent with some embodiments, a computer-assisted medical device includes a control unit comprising one or more processors, a first articulated arm including one or more first joints, a second articulated arm including one or more second joints, and an arm stabilizer. The arm stabilizer includes a spine, a first vibration absorbing mount attached to the spine, a second vibration absorbing mount attached to the spine, a first clamp attached to the first vibration absorbing mount, and a second clamp attached to the second vibration absorbing mount. The first clamp holds a first attachment point on the first articulated arm without slipping. The second clamp holds a second attachment point on the second articulated arm without slipping. The arm stabilizer stabilizes and reduces vibration in the first and second articulated arms.

Consistent with some embodiments, a method of controlling motion of a medical tool includes determining a first pose for a first medical tool attached to a distal end of a first articulated arm of a computer-assisted medical device, determining a second pose for a second medical tool attached to a distal end of a second articulated arm of the computer-assisted medical device, deploying the first and second articulated arms so that a first attachment point on the first articulated arm and a second attachment point of the second articulated arm are positioned and oriented relative to each other based on a size and a shape of an arm stabilizer, attaching the arm stabilizer to the first and second attachment points using respective clamps, positioning and orienting the first medical tool based on the first pose, and positioning and orienting the second medical tool based on the second pose. The arm stabilizer stabilizes and reduces vibration in the first and second articulated arms.

Consistent with some embodiments, a non-transitory machine-readable medium includes a plurality of machine-readable instructions which when executed by one or more processors associated with a medical device are adapted to cause the one or more processors to perform a method. The method includes determining a first pose for a first medical tool attached to a distal end of a first articulated arm of a computer-assisted medical device, determining a second pose for a second medical tool attached to a distal end of a second articulated arm of the computer-assisted medical device, deploying the first and second articulated arms so that a first attachment point on the first articulated arm and a second attachment point of the second articulated arm are positioned and oriented relative to each other based on a size and a shape of an arm stabilizer, attaching the arm stabilizer to the first and second attachment points using respective clamps, positioning and orienting the first medical tool based on the first pose, and positioning and orienting the second medical tool based on the second pose. The arm stabilizer stabilizes and reduces vibration in the first and second articulated arms.

BRIEF DESCRIPTION OF THE DRAWINGS

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Computer-assisted systems with one or more articulated arms, end effectors, and/or imaging devices (such as endoscopes) provide great flexibility to the operating room and/or interventional suite. By providing computer control over the movement, position, and/or orientation of the articulated arms and/or the end effectors, it is possible for the computer-assisted system to provide significant advantages to both patients and medical personnel during medical procedures. In some examples, the computer-assisted systems may take advantage of information in both pre-operative and intra-operative images to help position and/or orient the end effectors and/or devices attached to the end effectors to desired positions within a patient's anatomy.

In some embodiments, an articulated arm, end effector, and/or imaging device (such as an endoscope) used to manipulate and/or visualize a medical tool tip may not provide sufficient stability to the tool tip and/or captured images to support a desired medical procedure. Further, in some examples, the articulated arm, end effector, and/or imaging device (such as an endoscope) may be subject to oscillations and/or vibrations that may interfere with use of the tool tip. In some examples, a sufficiently thick body wall of the patient may be used to compensate for these stability and/or vibrations issues as the body wall may be able to stabilize and/or absorb vibrations via the cannula through which the medical tool is inserted into the patient. For minimally invasive medical procedures where there is a non-compliant body wall supporting the cannula (e.g., through the ribs in cardiac and thoracic procedures), a non-circumferential retainer on the cannula (e.g., procedures where multiple cannulas go through the same larger incision such as transaxial thyroidectomy), a thin or frail body wall (e.g. pediatric or elderly patients), or no constraint/body wall at all (e.g., transoral, transanal, transvaginal, eye surgery, or extremity reconstructive procedures) the body wall alone may not be able to provide sufficient stabilization and/or vibration absorption to support many medical procedures where precision is important.

In some embodiments, these limitations may be adequately mitigated by using two or more articulated arms to steady each other. For example, by connecting two articulated arms together at or near their distal ends near the medical tools they are manipulating (e.g., at a suitable point on the medical tools, imaging devices, and/or the end effectors holding the medical tools) a closed kinematic chain may be formed using the two articulated arms. In some examples, the closed kinematic chain may improve the precision and/or accuracy in the positioning and/or orientation of the respective medical tools, such as in systems that depend on a kinematically-controlled remote center of motion. In some examples, stabilizing the remote center of motion may stabilize the motions of the instruments, reduce friction between the tool/cannula interface, and/or improve precision and/or accuracy during a procedure. In some examples, a closed kinematic chain may also allow each of the articulated arms to stabilize the other and/or allow each of the articulated arms to help dampen and/or remove the vibrations of the other.

In some embodiments, additional benefits may be realized by connecting the two articulated arms together by using an arm stabilizer. In some examples, the arm stabilizer may be used to obtain reproducible port placements on procedures where spacing is difficult. In some examples, the arm stabilizer may decrease surgical system vibrations by coupling the articulated arms together, thereby effectively grounding the masses of the articulated arms. In some examples, the arm stabilizer may decrease local vibrations on each of the articulated arms and thereby increase the precision and/or accuracy of the articulated arm that is moving. In some examples, the arm stabilizer may help support the remote center of motion by decreasing friction between an end effector, an instrument shaft, and/or imaging device and a cannula through which it is inserted. In some examples, the arm stabilizer may support additional motion control applications that would otherwise rely on the body wall constraint, such as compensation for surgical table motion and/or the like. In some examples, the arm stabilizer may allow for improved port placement reproducibility for procedures where a tight or complicated port placement pattern is desired. In some examples, the arm stabilizer may reduce the minimum spacing (e.g., about 4 mm) between articulated arms that is maintained to prevent external collisions. In some examples, the arm stabilizer may support gravity compensation for procedures where there is no body wall constraint, such as during transoral, transanal, transvaginal, eye surgery, and/or reconstructive extremity surgery.

Figure 1A:
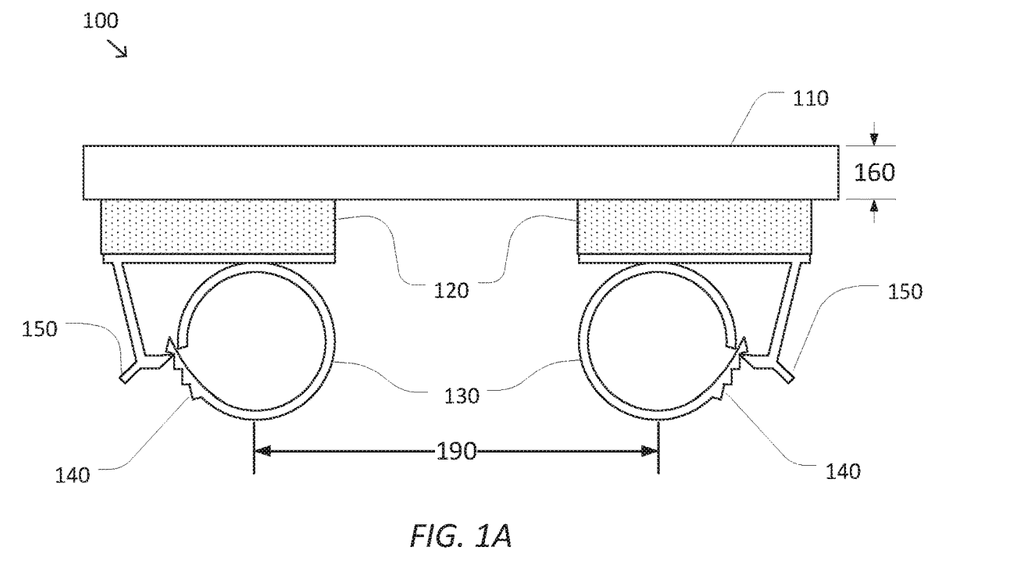
FIGS. 1A and 1B are simplified diagrams of a top and side view of an arm stabilizer for use with two articulated arms and/or end effectors according to some embodiments.
Figure 1B:
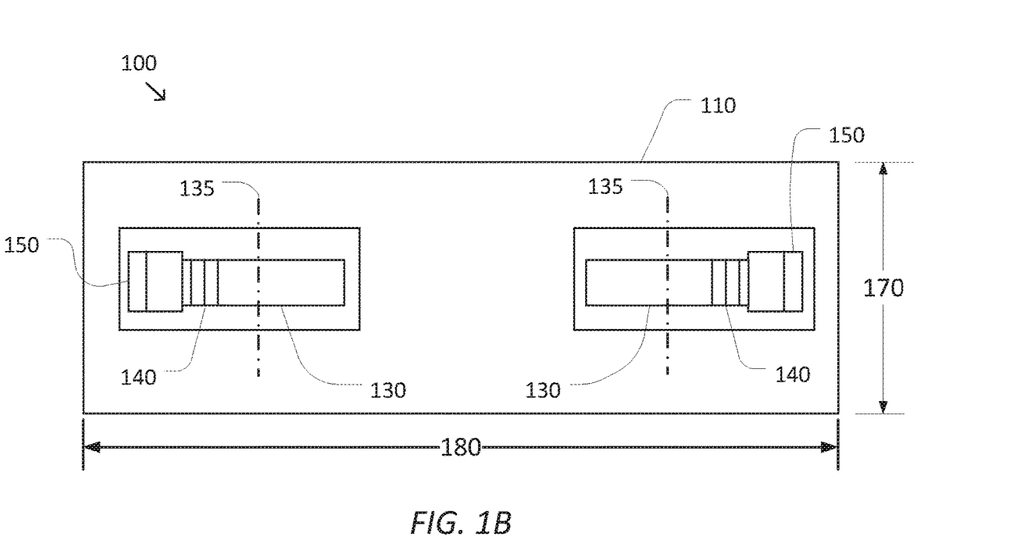

FIGS. 1A and 1B are simplified diagrams of a top and side view of an arm stabilizer 100 for use with two articulated arms and/or end effectors according to some embodiments. As shown in FIGS. 1A and 1B, arm stabilizer 100 includes a rigid or semi-rigid spine 110. Mounted to spine 110 via respective vibration-absorbing mounts 120 are two clamps 130. As shown, the mounts 120 and clamps 130 are at opposite ends of spine 110, and in other embodiments, the mounts and clamps may be at other locations along the spine, or may be movable along the spine from one fixed position to another fixed position. Two clamps 130 are shown, and additional clamps may be added. Clamps may be on the same side of the spine as shown, or they may be on obverse and reverse sides of the spine. Each of the clamps 130 is adapted to hold a suitable portion of a respective articulated arm, end effector, and/or medical tool with a non-slip grip. In some examples, each of the clamps 130 is designed to open so that the respective articulated arm, end effector, medical tool, and/or cannula may be placed inside the clamp 130 from the side without having to insert the articulated arm, end effector medical tool, and/or cannula through a closed portion of the clamp 130 along a direction of a central axis 135 of the clamp 130. In some examples, the use of clamps 130 that open with articulated arms, end effectors, medical tools, imaging devices, and/or cannulas that are larger around than the clamps 130 at points on the articulated arms, end effectors, medical tools, and/or cannulas that are distal to the clamps 130.

As shown in the examples of FIGS. 1A and 1B, each of the clamps 130 is a ratcheting-style clamp with ratchet teeth 140 that may be held in place by a handle 150, by which the ratchet teeth 140 are passed as the clamp 130 is tightened. As further shown in the examples, the handle 150 may include a quick-release feature that allows the handle 150 to be quickly disengaged from the ratchet teeth 140, thus allowing the clamp 130 to be easily removed from the articulated arm, end effector, medical tool, and/or cannula. In some examples, the clamps 130 may be manufactured using a flexible material, such as nylon, that facilitates the opening and closing of the clamps 130 and/or adjusting the cross-sectional size of the clamps 130 to account for variations in the size and/or shape of the articulated arms, end effectors, medical tools, and/or cannulas being held by the clamps 130. In some example, the flexible material may also help prevent damage to the clamped medical device component (the clamped object). In some examples, an interior surface of the clamps 130 may be lined with an elastomeric material (not shown) to further improve the ability of the clamps 130 to hold articulated arms, end effectors, medical tools, and/or cannulas of varying sizes and/or shapes. In some examples, the elastomeric material may also be used to help dampen vibrations due to shear forces and/or torques between the clamp and the clamped object. In some examples, the elastomeric material may further reduce the likelihood of the clamps damaging the articulated arms, end effectors, medical tools, and/or cannulas. In some examples, the elastomeric material may include rubber, neoprene, and/or the like.

In some embodiments, the combination of materials used in the spine 110 and the vibration-absorbing mounts 120 may improve the stability of and/or reduce vibration in the articulated arms, end effectors, medical tools, and/or cannulae being held by the clamps 130. In some examples, the spine 110 may be used to improve the stability of the articulated arms, end effectors, medical tools, and/or cannulae being held by the clamps 130. In some examples, a thickness 160 and a height 170 of the spine 110 may be selected to provide sufficient stiffness to the arm stabilizer 100 so as to limit relative motion between the articulated arms, end effectors, medical tools, and/or cannulae being held by the clamps 130 and/or resist, with little or no deformation, forces and/or torques placed on the arm stabilizer 100 by the articulated arms, end effectors, medical tools, and/or cannulae being held by the clamps 130 while helping to reduce the forces and/or torques. In some examples, by stabilizing the remote center of motion of the clamped object, the cannula may be less likely to bend, the remote center of motion is stabilized with reference to the patient, and/or the friction between the tool/cannula interface may be minimized while preserving instrument precision. In some examples, the spine 110 may be composed of one or more plastics, such as ABS, polycarbonate, polyethylene, polystyrene, and/or the like. In some examples, the spine 110 may be composed of a material with a Young's Modulus in a range from 1 to 5 GPa. In some examples, the height 170 may be between 4 cm and 6 cm. In some examples, the thickness 160 may be between 2 mm and 3 cm. In some examples, the spine 110 may have a shape other than the rectangular shape shown in FIGS. 1A and 1B.

In some examples, the vibration-absorbing mounts 120 may be used to reduce undesirable oscillations and/or vibrations in the articulated arms, end effectors, medical tools, and/or cannulae being held by the clamps 130. In some examples, the vibration-absorbing mounts 120 may be composed of one or more vibration-absorbing materials designed to dampen vibrations of one or more frequencies between 0.5 and 14 Hz. In some examples, the vibration-absorbing mounts 120 may have a medium-soft durometer, such as an ASTM D2240 Shore A durometer between 30 and 70. In some examples, the vibration-absorbing material may be rubber, ISOdamp C-1002 manufactured by EAR Specialty Composites of Indianapolis, Indiana, and/or the like.

In some examples, the vibration-absorbing mounts 120 may be mounted to the spine 110 and the clamps 130 using any suitable adhesive with sufficient holding strength with the materials from which the spine 110, the vibration-absorbing mounts 120, and the clamps 130 are composed. In some examples, the adhesive may include Super Glue, an epoxy, Loctite® 380™, an adhesive resin, and/or the like. In some examples, mechanical mounting may also be used.

In some embodiments, a width 180 of the spine 110 may be chosen to contribute to stiffness of the arm stabilizer 110 as well as to maintain a desired separation distance 190 between centers of the clamps 130. In some examples, the separation 190 may be chosen to provide sufficient separation between the articulated arms, end effectors, medical tools, and/or cannulae being held by the clamps 130 to reduce the likelihood of collisions between the articulated arms, end effectors, medical tools, and/or cannulas and/or to provide a suitable separation between the medical tools to support a medical procedure being performed. In some examples, the separation 190 may be sufficient to allow the use of an imaging device, such as an endoscope, adjacent to the region between the two clamps 130. In some examples, the separation distance 190 may be between 4 cm and 10 cm.

In some embodiments, positions of the clamps 130 and/or the vibration-absorbing mounts 120 may be adjustable to vary the separation 190 based on variations in a patient's anatomy and/or a procedure being performed while using the arm stabilizer 110. In some examples, the clamps 130 and/or vibration-absorbing mounts 120 may be mounted on an adjustable track and/or similar feature to allow movement of one or both of the clamps 130 relative to the spine 110. In some examples, the adjustable track may include one or more sensors for determining the separation 190. In some examples, suitable position sensors include electrical, magnetic, and optical technology sensors. In some examples, one or more sensors may be read by the computer-assisted medical device being used with the arm stabilizer 100.

In some embodiments, the relative orientation of the clamps 130 may be adjusted. In some examples, the central axis 135 of each of the clamps 130 may be parallel to each other so that the links of the articulated arms, end effectors, tool tips, and/or cannulas being held by the clamps 130 may be kept parallel to each other which the arm stabilizer 100 is being used. In some examples, the central axes 135 may be splayed relative to each other so that either the distal ends of the links of the articulated arms, end effectors, tool tips, and/or cannulas being held by the clamps 130 may be angled toward or away from each other. In some examples, orientation of the clamps 130 to the spine 110 may be adjustable using respective rotational joints (not shown) between the clamps 130 and the vibration-absorbing mounts 120 and/or between the vibration-absorbing mounts 120 and the spine 110. In some examples, the rotational joints may be lockable in a fixed orientation. In some examples, the rotational joints may include one or more sensors that may be used to determine a relative angle between the central axes 135 and/or the rotational angles of the rotational joints. In some examples, suitable position sensors include electrical, magnetic, and optical technology sensors. In some examples, one or more sensors may be read by the computer-assisted medical device being used with the arm stabilizer 100.

In some embodiments, the relative orientations between the clamps 130 and the spine 110 are designed to minimize a cross section occupied by the spine 110 when viewed along the direction of central axes 135 of the clamps 130. In some examples, this relative orientation may allow for a larger spine 110 while reducing any obstruction the arm stabilizer 100 introduces when viewed by users and/or imaging devices taking images along the direction toward the distal ends of the articulated arms, end effectors, medical tools, and/or cannulas being held by the clamps 130. In some examples, use of the larger spine 110 may allow the arm stabilizer 100 to provide greater stiffness and/or stabilization to the articulated arms, end effectors, medical tools, imaging devices, and/or cannulas being held by the clamps 130.

In some embodiments, each of the clamps 130 may include suitable identifying features so the articulated arm, end effector, medical tool, and/or cannula begin held by the clamp 130 may identify the clamp 130 as belonging to arm stabilizer 100 and may further identify a model number of arm stabilizer 100. In some examples, the identifying features may include one or more physical patterns, electrical contacts, magnets, RFID devices, and/or the like.

In some embodiments, arm stabilizer 100 may further include a memory device (not shown). In some examples, the memory device may be used to store information associated with arm stabilizer 100, including arm stabilizer type, arm stabilizer identification number, arm stabilizer model number, arm stabilizer kinematic parameters, and/or the like. In some examples, the stored information may be read by the computer-assisted system upon attachment of either of the clamps 130 to one of the articulated arms, end effectors, medical tools, and/or cannulae. In some examples, the read information may be used by the computer-assisted system to identify arm stabilizer 100, set control parameters, access the kinematic parameters, and/or the like in order to more effectively operate the computer-assisted system. In some examples, the memory device may be accessed using the electrical contacts, RF communication, and/or the like. In some examples, the memory device may include a machine-readable medium, such as RAM, PROM, EPROM, FLASH-EPROM, any other memory chip or cartridge, and/or any other medium from which a processor or computer is adapted to read.

As discussed above and further emphasized here, FIGS. 1A and 1B are merely examples which should not unduly limit the scope of the claims. One of ordinary skill in the art would recognize many variations, alternatives, and modifications. According to some embodiments, other types of clamps may be used. In some examples, the ratcheting clamp 130 may be replaced by a snap-in clamp, a spring-loaded clamp, Velcro® or similar hook and loop type fastener and/or other strapping, and/or the like. In some examples, the clamps 130 may have cross-sectional shapes other than approximately circular, such as ovoid, hexagonal, octagonal, and/or other polygonal shapes and the like. In some examples, the cross-sectional shape of the clamps may depend on a corresponding cross-sectional shape attachment points of the articulated arms, end effectors, medical tools, and/or cannulas being clamped.

In some embodiments, the vibration-absorbing mounts 120 may be arranged in other than the two separate mounts shown in FIG. 1A. In some examples, the vibration-absorbing mounts 120 may be a single mount. In some examples, each of the vibration-absorbing mounts 120 may include several smaller sections of vibration-absorbing material so that each of the clamps 130 is mounted to the spine 110 using the several smaller sections of vibration-absorbing material. In some examples, the spine 110 may be conformally coated with, or may otherwise include, a vibration-absorbing material in place of the separate vibration-absorbing mounts 120.

Figure 2:
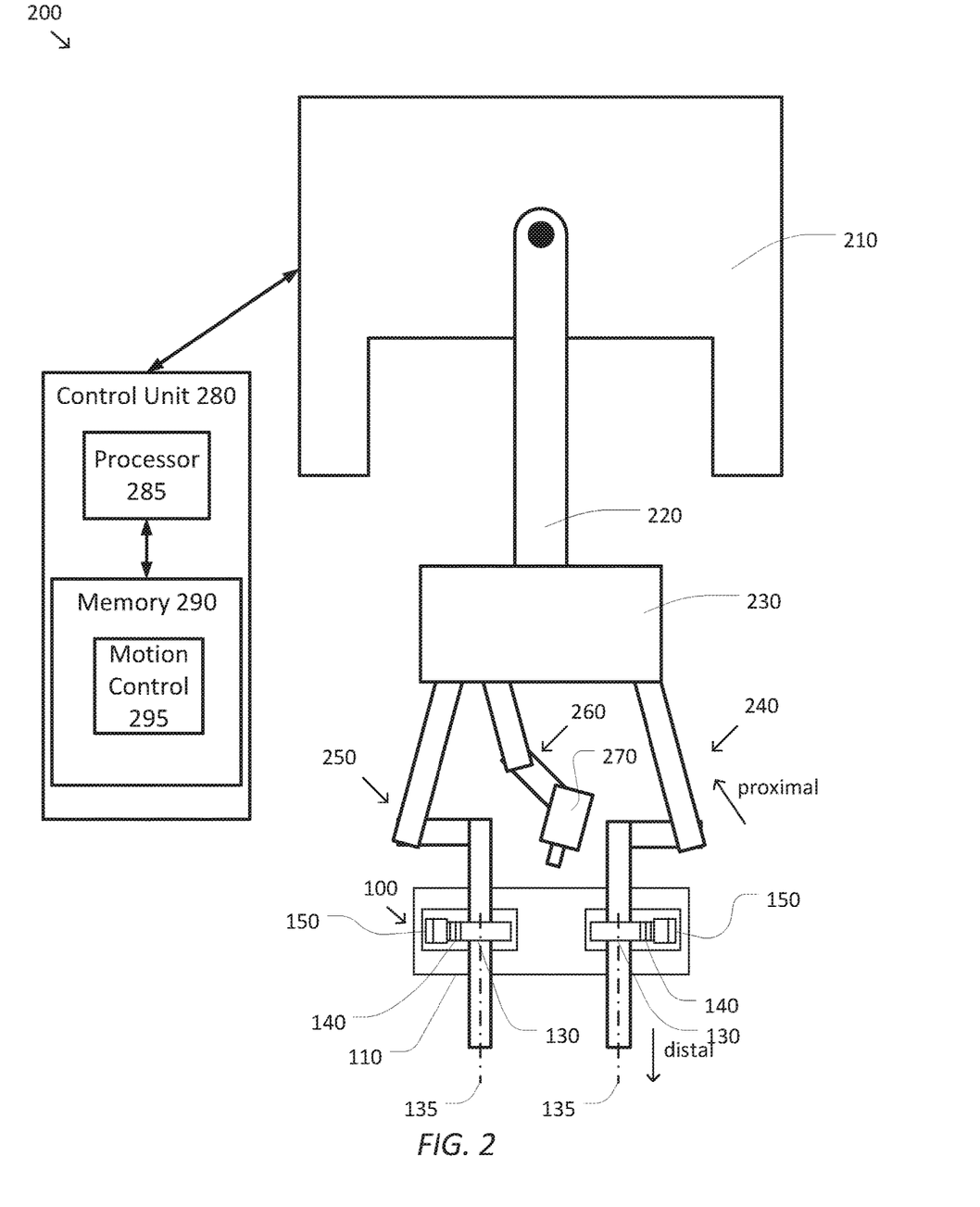
FIG. 2 is a simplified diagram of a computer-assisted system according to some embodiments.

FIG. 2 is a simplified diagram of a computer-assisted system 200 according to some embodiments. As shown in FIG. 2, computer-assisted system 200 includes a computer-assisted medical device supporting multiple articulated arms. In some embodiments, the computer-assisted medical device and an operator workstation (not shown) may correspond to a da Vinci® Surgical System commercialized by Intuitive Surgical, Inc. of Sunnyvale, California. The computer-assisted medical device includes a base 210. In some examples, base 210 may include one or more wheels and/or may be mounted on a track to facilitate positioning of the computer-assisted medical device within an operating room, interventional suite, and/or adjacent to a patient table. To facilitate positioning of the articulated arms of the computer-assisted medical device, a set-up structure 220 may be mounted on base 210. The set-up structure 220 may include one or more joints and/or links that may be used to adjust a position, orientation, and/or height of an articulated arm gantry 230. In some examples, gantry 230 may be positioned over a patient table. In some examples, set-up structure 220 may further include one or more sensors and/or the like to allow computer-assisted system 200 to determine a forward and/or inverse kinematic transform characterizing the position and/or orientation of gantry 230 relative to base 210. In some examples, set-up structure 220 may further include one or more actuators and/or the like to allow computer-assisted system 200 to change the position and/or orientation of gantry 230 relative to base 210 and set-up structure 220.

Attached to gantry 230 are several articulated arms 240, 250, and 260. And although FIG. 2 shows three articulated arms 240, 250, and 260 attached to gantry 230, other configurations may include only two articulated arms, and additional articulated arms may also be present. Each of the articulated arms 240, 250, and 260 may include one or more joints and links between the proximal end attached to gantry 230 and the distal end to which a respective end effector, tool, imaging device, cannula, medical tool, and/or the like are attached. In some examples, each of the articulated arms 240, 250, and 260 may further include one or more sensors and/or the like to allow computer-assisted system 200 to determine a forward and/or inverse kinematic transform characterizing the position and/or orientation of the distal end of the respective articulated arm 240, 250, and/or 260 relative to gantry 230. In some examples, each of the articulated arms 240, 250, and 260 may further include one or more sensors for determining forces and/or torques being applied to the joints and/or links of the respective articulated arm 240, 250, and/or 260. In some examples, each of the articulated arms 240, 250, and 260 may further include one or more actuators and/or the like to allow computer-assisted system 200 to change the position and/or orientation of respective end effectors at the distal ends of each of the articulated arms 240, 250, and 260 relative to gantry 230.

As shown in FIG. 2, an arm stabilizer 100 is attached near the distal ends of the articulated arms 240 and 250. A respective link in each of the articulated arms 240 and 250 is inserted into a corresponding clamp 130 of the arm stabilizer 100. In some examples, the respective link may correspond to a link in the articulated arm 240 or 250, an end effector mounted at the distal end of articulated arm 240 or 250, a medical tool mounted at the distal end of articulated arm 240 or 250, and/or a cannula for use at the distal end of articulated arm 240 or 250. In some examples, respective ratchet teeth 140 and handle 150 may be used to tighten the each of the clamps 130 around the respective links at corresponding attachment points. The attachment of the arm stabilizer 100 to the articulated arms 240 and 250 creates a closed kinematic loop between gantry 230, through articulated arm 240, the clamps 130, vibration-absorbing mounts 120, and spine 110 of the arm stabilizer 100, through articulated arm 250, and back to gantry 230. In some examples, the closed kinematic loop may be used to provide stability in the position and/or orientation of the distal ends of the articulated arms 240 and/or 250 over and/or near target anatomy of a patient. In some examples, the closed kinematic loop may be used to provide higher stiffness for the articulated arms 240 and/or 250 relative to the stiffness of a single articulated arm.

As further shown in FIG. 2, an imaging device 270 may be attached to the distal end of articulated arm 260. In some examples, imaging device 270 may be an endoscope, an ultrasound device, and/or the like suitable for insertion into the patient. In some examples, imaging device 270 may provide one or more images of the target anatomy to facilitate the positioning, orientation, and/or use of the medical tools mounted at the distal ends of the articulated arms 240 and 250. In some examples, when imaging device 270 includes stereoscopic and/or other three-dimensional imaging capabilities, imaging device 270 may be used to determine a kinematic relationship between gantry 230 and the target anatomy. In some examples, this kinematic relationship may be useful in positioning and/or orienting the medical tools mounted at the distal ends of the articulated arms 240 and 250 relative to the target anatomy. In some examples, the relative thinness of the thickness 160 of the spine 110 may help minimize any obstruction that the spine 110 and the arm stabilizer 100 introduce in the images provided by imaging device 270 because a cross-section of the spine 110 along the direction of view of imaging device 270 is generally limited to an area defined by the thickness 160 and the width 180.

The computer-assisted medical device is coupled to a control unit 280 via an interface. The interface may include one or more cables, connectors, and/or buses and may further include one or more networks with one or more network switching and/or routing devices. Control unit 280 includes a processor 285 coupled to memory 290. Operation of control unit 280 is controlled by processor 285. And although control unit 280 is shown with only one processor 285, it is understood that processor 285 may be representative of one or more central processing units, multi-core processors, microprocessors, microcontrollers, digital signal processors, field programmable gate arrays (FPGAs), application specific integrated circuits (ASICs), and/or the like in control unit 280. Control unit 280 may be implemented as a stand-alone subsystem and/or board added to a computing device or as a virtual machine. In some embodiments, control unit 280 may be included as part of the operator workstation for allowing medical personnel to control and/or operate computer-assisted system 200. In some examples, control unit 280 may be operated separately from, but in coordination with the operator workstation.

Memory 290 may be used to store software executed by control unit 280 and/or one or more data structures used during operation of control unit 280. Memory 290 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 290 includes a motion control application 295 that may be used to support autonomous and/or semiautonomous control of computer-assisted system 200. Motion control application 295 may include one or more application programming interfaces (APIs) for receiving position, motion, and/or other sensor information from the sensors in set-up structure 220, the articulated arms 240, 250, and/or 260, and/or the arm stabilizer 100 as will be discussed in further detail below. In some examples, motion control application 295 may receive one or more pre-operative images, intra-operative images, images from imaging device 270, and/or the like as will be discussed in further detail below. In some examples, motion control application 295 may support the autonomous and/or semi-autonomous motion of articulated arms 240, 250, and/or 260 to help position and/or orient the medical tools mounted at the distal ends of the articulated arms 240 and/or 250 as will be discussed in further detail below. In some examples, motion control application 295 may also exchange position, motion, and/or collision avoidance information with other control units regarding other devices, and/or planning and/or assisting in the planning of motion for computer-assisted system 200, articulated arms 240, 250, and/or 260, and/or the like. And although motion control application 295 is depicted as a software application, motion control application 295 may be implemented using hardware, software, and/or a combination of hardware and software.

Figure 3:
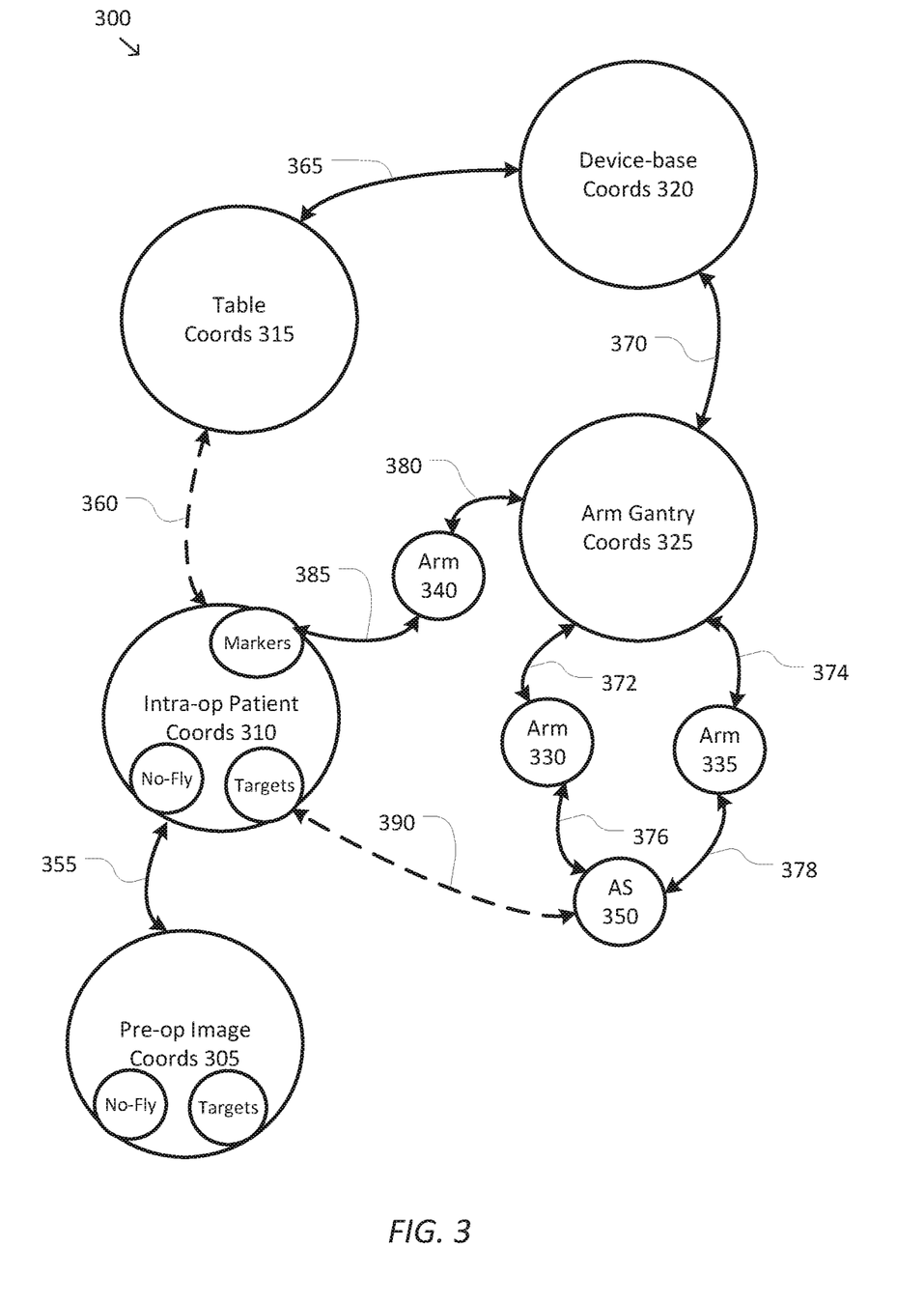
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. In some embodiments, before a medical procedure is performed, it is common for one or more pre-operative images to be obtained. In some examples, these pre-operative images may include a series of tomographic images that may be used to develop a three-dimension model of the patient's anatomy. In some examples, the pre-operative images may be taken via computed tomography (CT), magnetic resonance imaging (MRI), and/or the like. In some examples, medical personnel may review the pre-operative images to develop a plan for a medical procedure that may identify one or more targets and/or other points of interest in the patient's anatomy. In some examples, the plan may also identify one or more no-fly zones that may be used to protect patient anatomy during the medical procedure. In some examples, the pre-operative images, as well as the targets and/or no-fly zones may be established in a pre-operative image coordinate system 305. In some examples, the pre-operative image coordinate system 305 may be determined in part by a coordinate system and/or one or more kinematic models associated with the one or more imaging devices taking the pre-operative images.

In some embodiments, once the patient is positioned and oriented for the medical procedure, one or more intra-operative images may be obtained to determine the position and/or orientation of the patient for the medical procedure. In some examples, the intra-operative images may include two or more X-rays obtained along non-parallel axes. In some examples, the non-parallel axes may have an angular separation of at least 30 degrees. In some examples, the X-ray images may be lateral and anterior-posterior images of the patient. In some examples, the intra-operative images may use other imaging technology that identifies three-dimensional information and may include ultrasound, bi-plane fluoroscopy, stereoscopic fluorescence imaging, and/or the like. In some examples, an intra-operative patient coordinate system 310 may be determined in part by a coordinate system and/or one or more kinematic models associated with the one or more imaging devices taking the intra-operative images.

In some embodiments, medical personnel may review the intra-operative images to determine positions of the targets identified as part of the plan using the pre-operative images. In some examples, one or more no-fly zones may also be identified in the intra-operative images. In some examples, positions of one or more markers and/or identified anatomical features may be located using the intra-operative images. In some examples, the intra-operative images, as well as the targets, no-fly zones, features, and/or markers may be established in the intra-operative patient coordinate system 310.

In some embodiments, the patient may be located on a patient table that may be positioned and/or oriented by medical personnel. In some examples, a height of the patient table above the floor may be adjusted. In some examples, an orientation of the patient table may be adjusted along one or more roll, pitch, yaw, and/or the like axes. In some examples, the position and/or orientation of the patient table may be established in a table coordinate system 315.

In some embodiments, a computer-assisted medical device, such as the computer-assisted medical device of FIG. 2, may be used during the medical procedure. In some examples, the position and/or orientation of a base of the computer-assisted medical device may be adjusted relative to the patient table. In some examples, the computer-assisted medical device may be established in a device-base coordinate system 320.

In some embodiments, the computer-assisted medical device may include a set-up structure, such as set-up structure 220, to adjust a position and orientation of a gantry to which one or more articulated arms are attached. In some examples, the gantry may be similar to gantry 230. In some examples, the gantry may be established in an arm gantry coordinate system 325.

In some embodiments, a plurality of articulated arms may be attached to the gantry. Each of the articulated arms may include one or more joints and/or links with the joints and/or links establishing a coordinate system 330, 335, and/or 340 at a distal end of each of the articulated arms and/or an end effector at the distal end of a respective articulated arm. In some examples, the articulated arms associated with arm coordinate systems 330 and 335 may correspond to articulated arms 240 and 250 and the articulated arm associated with arm coordinate system 340 may correspond to articulated arm 260.

In some embodiments, an arm stabilizer, such as arm stabilizer 100, may be used to hold the articulated arms associated with arm coordinate systems 330 and 335. In some examples, positions and/or orientation of clamps on the arm stabilizer may be established in an arm stabilizer coordinate system 350. In some examples, the positions and/or orientations of the clamps on the arm stabilizer may be determined based on a kinematic model of the arm stabilizer and/or based on sensors in the adjustable track and/or rotational joints used to adjust the positions and/or orientations of the clamps.

In some embodiments, an imaging device may be coupled to the distal end of the articulated arm associated with arm coordinate system 340. In some examples, the imaging device may be an endoscope, an ultrasound device, a microscope, and/or the like. In some examples, the imaging device may include stereoscopic and/or other three-dimensional positioning capabilities for mapping observed images to arm coordinate system 340.

In some embodiments, kinematic modeling and/or one or more registration processes may be used to establish the kinematic relationships between the various coordinate systems 305-350. In some examples, the kinematic modeling and/or registration processes may be used to establish transformation matrices between the various coordinate systems 305-350 to permit the forward and/or reverse mapping of positions and/or orientations in one of the coordinate systems 305-350 to another of the coordinate systems 305-350.

In some embodiments, a registration process may be used to determine a pre-operative to intra-operative kinematic relationship 355 between the pre-operative coordinate system 305 and the intra-operative patient coordinate system 310. In some examples, the registration process may include identifying common image elements in the pre-operative and intra-operative images (e.g., unique and/or unusual anatomical features, markers, and/or the like), locating the common image elements in both the pre-operative image and intra-operative patient coordinate systems 305, 310, and using the differences between the positions and/or orientations of the common image elements to determine the translations, scales, and/or rotations between the pre-operative image coordinate system 305 and the intra-operative coordinate system 310. The translations, scales, and/or rotations may be used to determine the pre-operative to intra-operative kinematic relationship 355. In some examples, the pre-operative to intra-operative kinematic relationship 355 may be used to transform the targets and/or no-fly zones identified during the pre-operative plan from the pre-operative image coordinate system 305 to the intra-operative patient coordinate system 310. In some examples, the pre-operative to intra-operative kinematic relationship 355 may include multiple transformations that apply to sub-regions within the pre-operative and intra-operative coordinate systems 305 and 310 to account for changes in the patient's anatomy between a pose used for the pre-operative images and the pose used for the intra-operative images. In some examples, the sub-regions may account for changes in positions of the patient's joints, vertebrae, and/or the like between the pre-operative and intra-operative poses.

In some embodiments, a patient to table kinematic relationship 360 between the patient (i.e., the intra-operative patient coordinate system 310) and the patient table (i.e., the table coordinate system 315) may not be directly determined. However, a closed kinematic chain may be used to determine the patient to table kinematic relationship 360 as is discussed in further detail below.

In some embodiments, a table to device-base kinematic relationship 365 may be determined using a registration process between the patient table and the computer-assisted medical device. Methods and approaches for establishing the table to device-base kinematic relationship are described in greater detail in U.S. patent application Ser. No. 61/954,538, (filed Mar. 17, 2014) (entitled "Methods and Systems for Tele-Surgical Table Registration"), which is hereby incorporated by reference for all purposes.

In some embodiments, a set-up structure kinematic relationship 370 between the device-base coordinate system 320 and the arm gantry coordinate system 325 may be determined by using one more kinematic models of the set-up structure coupling the device base to the gantry. In some examples, one or more sensors located in the set-up structure may be used to determine the coordinate transformation associated with the set-up structure kinematic relationship 370. In some examples, the set-up structure kinematic relationship 370 may be updated as the gantry is moved to different positions and/or orientations relative to the device base coordinate system 320.

In some embodiments, corresponding articulated arm kinematic relationships 372 and 374 between the arm gantry coordinate system 325 and the articulated arm coordinate systems 330 and 335, respectively, may be determined by using one or more kinematic models of the articulated arms and/or end effectors coupling the gantry to a distal end of the corresponding articulated arms and/or end effectors. In some examples, one or more sensors located in the articulated arms and/or end effectors may be used to determine the coordinate transformation associated with the corresponding articulated arm kinematic relationships 372 and 374. In some examples, the articulated arm kinematic relationships 372 and 374 may be updated as the articulated arms and/or end effectors are moved to different positions and/or orientations relative to the arm gantry coordinate system 325.

In some embodiments, corresponding arm stabilizer kinematic relationships 376 and 378 between the respective arm coordinate systems 330 and 335 and the arm stabilizer coordinate system 350 may be determined by using the closed kinematic loop through the arm stabilizer and the kinematics of the clamps (e.g., clamps 130), vibration-absorbing mounts (e.g., vibration-absorbing mounts 120), and spine (e.g., spine 110) of the arm stabilizer. In some examples, the articulated arm kinematic relationships 372 and 374 may be used to determine a position and an orientation of the points on the articulated arms, end effectors, medical tools, and/or cannulas to which the clamps of the arm stabilizer are attached in the same articulated arm coordinate system 330 or 335. Consider the case where the articulated arm coordinate system 330 is selected as the coordinate system for determining the arm stabilizer kinematic relationships 376 and 378. The attachment point to the articulated arm associated with the articulated arm coordinate system 330 is known by the kinematics of that articulated arm. The position and orientation of the connection point of the arm stabilizer to the articulated arm associated with the articulated arm coordinate system 335 may be determined by combining the kinematic relationship 372 with the inverse of the kinematic relationship 374. Using the known kinematics of the arm stabilizer, it is possible to determine the arm stabilizer kinematic relationships 376 and 378. In some examples, the arm stabilizer kinematic relationships 376 and/or 378 may depend on current settings of any adjustable track and/or rotational joints of the arm stabilizer that may alter the distance between the clamps of the arm stabilizer and/or adjust a relative angle between central axes of the clamps.

In some embodiments, an articulated arm kinematic relationship 380 between the arm gantry coordinate system 325 and the articulated arm coordinate system 340 may be determined by using one or more kinematic models of the articulated arm and/or end effector coupling the gantry to a distal end of the articulated arm and/or end effector. In some examples, one or more sensors located in the articulated arm and/or end effector may be used to determine the coordinate transformation associated with the articulated arm kinematic relationship 380. In some examples, the articulated arm kinematic relationship 380 may be updated as the articulated arm and/or end effector are moved to a different position and/or orientation relative to the gantry coordinate system 325.

In some embodiments, when an imaging device coupled to the articulated arm associated with the articulated arm coordinate system 340 is able to observe the features and/or markers located in the intra-operative patient coordinate system 310, it is possible to determine a patient kinematic relationship 385 between the articulated arm coordinate system 340 and the anatomy of the patient. In some examples, image processing of one or more images obtained by the imaging device may be used to determine positions and/or orientations of the features and/or markers on the anatomy of the patient in articulated arm coordinate system 340 and, thus, determine the patient kinematic relationship 385. In some examples, the positions and/or orientations of the targets and no-fly zones regions in the intra-operative patient coordinate system 310 may be mapped to the articulated arm coordinate system 340 by using the patient kinematic relationship 385.

In some embodiments, a closed kinematic chain through the intra-operative patient coordinates 310, patient kinematic relationship 385, articulated arm coordinate system 340, articulated arm kinematic relationship 380, arm gantry coordinate system 325, one of the articulated arm kinematic relationships 372 or 374, a corresponding one of the articulated arm coordinate systems 330 or 335, a corresponding one of the arm stabilizer kinematic relationships 376 or 378, and the arm stabilizer coordinate system 350 may be used to determine a tool to target kinematic relationship 390 by suitable application of the inverse and forward kinematic relationships. In some examples, the tool to target kinematic relationship 390 may be used to quickly convert the position and orientation of the medical tools in the articulated arm coordinate systems 330 or 335 and/or the arm stabilizer coordinate system 350 to the intra-operative patient coordinate system 310 so as to effectively control the positioning and/or orientation of the medical tools relative to the target while avoiding the no-fly zones.

In some embodiments, the patient to table kinematic relationship 360 may also be determined using the closed kinematic loop through the table to device-base kinematic relationship 365, the set-up structure kinematic relationship 370, the articulated arm kinematic relationship 380, and the patient kinematic relationship 385.

In some embodiments, the various kinematic relationships 355-390 may also be used to support collision avoidance when using the computer-assisted medical device. In some examples, the kinematic relationships (e.g., kinematic relationships 372, 374, 376, 378, and/or 380) may be used to help avoid collisions between the various articulated arms, such as between the articulated arms held by the arm stabilizer and the articulated arm holding the imaging device used to establish the patient kinematic relationship 385. In some examples, the kinematic relationships (e.g., kinematic relationships 360-390) may be used to prevent the articulated arms, end effectors, medical tools, and/or cannulae from entering the no-fly zones in the intra-operative patient coordinate system 310 and/or the patient table.

Figure 4:
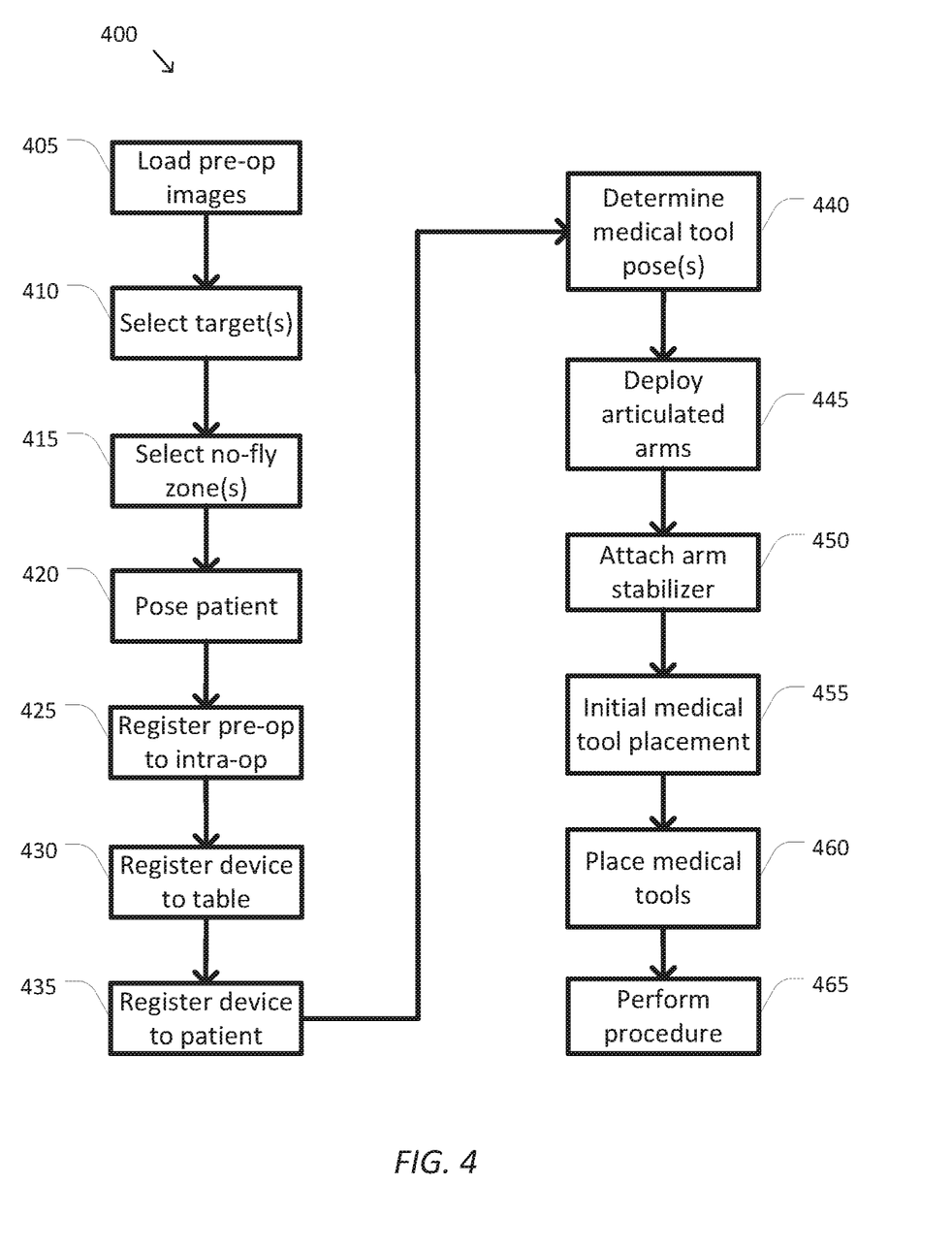
FIG. 4 is a simplified diagram of a method of arm stabilizer use according to some embodiments.

FIG. 4 is a simplified diagram of a method 400 of arm stabilizer use according to some embodiments. One or more of the processes 405-465 of method 400 may be implemented, at least in part, in the form of executable code stored on non-transient, tangible, machine-readable medium that when run by one or more processors (e.g., the processor 285 in control unit 280) may cause the one or more processors to perform one or more of the processes 405-465. In some embodiments, the method 400 may be performed by an application, such as motion control application 295. In some embodiments, processes 415, 430, and/or 455 are optional and may be omitted.

At a process 405, one or more pre-operative images are loaded. In some embodiments, a surgical plan is determined upon review of the one or more pre-operative images. In some examples, the one or more pre-operative images may be images of a desired portion of a patient's anatomy. In some examples, the one or more pre-operative images may include one or more slices and/or other three-dimensional information of the patient's anatomy. In some examples, the one or more pre-operative images may be obtained from a tomographic imaging device such as a CT, MRI, and/or similar imaging device. In some examples, the one or more pre-operative images may be associated with a pre-operative image coordinate system, such as pre-operative image coordinate system 305. During process 405, at least one of the pre-operative images is loaded for display to medical personnel.

At a process 410, one or more targets are selected. In some embodiments, the medical personnel may review the one or more pre-operative images loaded during process 405 to determine the one or more targets for a medical procedure. In some examples, the target may be selected using a pointing device on the pre-operative image loaded during process 405. In some examples, the one or more targets may be associated with one or more portions of a patient's anatomy that is to be the subject of the medical procedure. In some examples, the one or more targets may be located within the pre-operative image coordinate system.

At an optional process 415, one or more no-fly zones are selected. In some embodiments, the medical personnel may further review the one or more pre-operative images loaded during process 405 to determine one or more no-fly zones within the one or more pre-operative images. In some examples, the one or more no-fly zones may be selected using a pointing device on the pre-operative image loaded during process 450. In some examples, the one or more no-fly zones may correspond with one or more regions of the patient's anatomy, which are to be avoided by a computer-assisted surgical system and/or one or more medical tools. In some examples, the one or more no-fly zones may be located within the pre-operative image coordinate system.

At a process 420, the patient is posed. In some embodiments, the patient may be prepared for a medical procedure and then posed on a patient table. In some examples, once the patient is posed, the particular pose may be associated with an intra-operative patient coordinate system, such as intra-operative patient coordinate system 310. In some examples, the patient table may be associated with a table coordinate system, such as table coordinate system 315.

At a process 425, the one or more pre-operative images are registered to one or more intra-operative images. In some embodiments, once the patient is posed for the medical procedure during process 420, one or more intra-operative images may be obtained to determine the position and/or orientation of the patient for the medical procedure. In some examples, the intra-operative images may include two or more X-rays obtained along non-parallel axes. In some examples, the non-parallel axes may have an angular separation of at least 30 degrees. In some examples, the X-ray images may be lateral and anterior-posterior images of the patient. In some examples, the intra-operative images may use other imaging technology that identifies three-dimension information and may include ultrasound, bi-plane fluoroscopy, stereoscopic fluorescence imaging, and/or the like. In some examples, the one or more intra-operative images may be associated with the intra-operative patient coordinate system.

In some examples, the registration may be used to determine a pre-operative to intra-operative kinematic relationship, such as the intra-operative kinematic relationship 355 between the pre-operative coordinate system 305 and the intra-operative patient coordinate system 310. In some examples, the registration process may include automated and/or semi-automated identification of one or more common image elements in the one or more pre-operative images and the one or more intra-operative images (e.g., one or more unique and/or unusual anatomical features, markers, and/or the like), locating the one or more common image elements in both the pre-operative image and intra-operative patient coordinate systems, and using the differences between the positions and/or orientations of the one or more common image elements to determine the translations, scales, and/or rotations between the pre-operative image coordinate system and the intra-operative patient coordinate system. The translations, scales, and/or rotations may be used to determine the pre-operative to intra-operative kinematic relationship. In some examples, the pre-operative to intra-operative kinematic relationship may be used to transform the one or more targets selected during process 410 and/or the one or more no-fly zones selected during process 415 from the pre-operative image coordinate system to the intra-operative patient coordinate system. In some examples, the user may update the target position and/or the no-fly zones based on the intra-operative patient pose. In some examples, the pre-operative to intra-operative kinematic relationship may include multiple transformations that apply to sub-regions within the pre-operative and intra-operative coordinate systems to account for changes in the patient's anatomy between a pose used for the one or more pre-operative images loaded during process 405 and the pose used for the one or more intra-operative images. In some examples, the sub-regions may account for changes in positions of the patient's joints, and/or the like between the pre-operative and intra-operative poses.

At an optional process 430, a computer-assisted medical device is registered to the patient table. In some embodiments, a table to medical device kinematic relationship, such as the table to device-base kinematic relationship 365, may be determined using a registration process between the patient table and the computer-assisted medical device. Methods and approaches for establishing the table to medical device kinematic relationship are described in greater detail in U.S. patent application Ser. No. 61/954,538, incorporated by reference above.

At a process 435, the computer-assisted medical device is registered to the patient. In some embodiments, registering of the computer-assisted medical device with the patient may begin with the acquisition of one or more computer-assisted medical device based images. The one or more computer-assisted medical device based images may be obtained to determine the position and/or orientation of the patient relative to the computer-assisted medical device. In some examples, the one or more computer-assisted medical device based images may be obtained by using an imaging device mounted on the computer-assisted medical device. In some examples, the one or more computer-assisted medical device based images may be obtained using imaging device 270 mounted at the distal end of an articulated arm (e.g., articulated arm 260) of the computer-assisted medical device. In some examples, the image device may be an endoscope, an ultrasound device, and/or the like. In some examples, the one or more computer-assisted medical device based images may provide one or more images of the patient's anatomy associated with one or more features and/or targets with known coordinates in the intra-operative patient coordinate system.

In some examples, the registration may be used to determine a patient to computer-assisted medical device kinematic relationship, such as the patient kinematic relationship 385 between the intra-operative coordinate system 310 and the articulated arm coordinate system 340. In some examples, the registration process may include automated and/or semi-automated identification of the one or more features and/or targets in the one or more computer-assisted medical device based images and the one or more intra-operative and/or one or more pre-operative images and using the differences between the positions and/or orientations of the one or more features and/or targets to determine the translations, scales, and/or rotations between the intra-operative patient coordinate system and the articulated arm coordinate system. The translations, scales, and/or rotations may be used to determine the patient to computer-assisted medical device kinematic relationship. In some examples, the patient to computer-assisted medical device kinematic relationship may be used to transform the one or more targets selected during process 410 and/or the one or more no-fly zones selected during process 415 from the intra-operative patient coordinate system to the articulated arm coordinate system. In some examples, additional coordinate systems (e.g., coordinates systems 320, 325, 330, and/or 335) and their kinematic relationships (e.g., kinematic relationships 370, 372, 374, and/or 380) may be used to transform the one or more targets selected during process 410 and/or the one or more no-fly zones selected during process 415 from the intra-operative patient coordinate system to one or more of the additional coordinate systems.

At a process 440, one or more medical tool poses are determined. In some embodiments, once the computer-assisted medical device is registered to the patient during process 435, the poses (i.e., positions and orientations) of the one or more medical tools to be used during the medical procedure may be determined. In some examples, the various kinematic relationships of the computer-assisted medical device (e.g., kinematic relationships 370, 372, 374, and/or 380) along with the patient to computer-assisted medical device kinematic relationship may be used to determine the positions and/or orientations for the one or more medical tools relative to the one or more targets selected during process 410 without intersecting any of the one or more no-fly zones determined during process 415. In some examples, determination of the one or more medical tool poses may further include determining desired joint positions for the articulated arms and/or end effectors of the computer-assisted medical device that are used to manipulate the one or more medical tools. In some examples, determination of the one or more medical tool poses may be an iterative process in which one or more proposed medical tool poses are shown to medical personnel with the medical personnel being able to make adjustments to the proposed pose. In some examples, the one or more proposed medical tool poses may be shown to the medical personnel as an overlay on the one or more intra-operative images obtained during process 425, the one or more pre-operative images loaded during process 405, and/or the one or more computer-assisted medical device based images obtained during process 435.

At a process 445, the articulated arms that are to be held by the arm stabilizer are deployed. In some examples, positioning and/or orientation of the articulated arms that are to be held by the arm stabilizer may be a complex task that may not be practical either by manual manipulation of the articulated arms in a clutched mode and/or via teleoperation. In some examples, the computer-assisted medical system may plan and execute motion plans for the articulated arms that are to be held by the arm stabilizer so as to place them in a suitable position and/or orientation for attaching the arm stabilizer. In some examples, the suitable position and/or orientation may be approximately located where the medical tools attached to the distal ends of the articulated arms are to be posed as determined during process 440. In some examples, the suitable position and/or orientation may place the attachment points on the articulated arms approximately the same distance apart as the separation (e.g., separation 190) between the clamps of the arm stabilizer and to align the links with the orientations of central axes of the clamps. In some examples, the deployment plan may further include determining one or more collision avoidance paths with other articulated arms of the computer-assisted medical device (e.g., the articulated arm to which the imaging device of process 435 is mounted), the set-up structure of the computer-assisted medical device, the patient, and/or the like. In some examples, the deployment plan may also include planned motions to move the other articulated arms and/or the set-up structure of the computer-assisted medical device out of the way of the articulated arms that are to be held by the arm stabilizer. In some examples, during deployment, forces and/or torques in the articulated arms may be monitored in order to detect unforeseen collisions with other objects, personnel, and/or the like in the vicinity of the computer-assisted medical device. In some examples, the deployment may include activating one or more actuators in the articulated arms and/or the set-up structure of the computer-assisted medical device by controlling one or more voltages, currents, duty cycles, and/or the like. In some examples, the deployment may be triggered by medical personnel using an activation button located on one of the articulated arms, via an operator console, and/or the like.

At a process 450, the arm stabilizer is attached. In some embodiments, each of the clamps of the arm stabilizer is attached to the connection point of a corresponding one of the articulated arms. In some examples, the attaching of the arm stabilizer may include opening the clamps, placing the respective attachment points within the clamps, and tightening the clamps. In some examples, the attaching of the arm stabilizer may include one or more medical personnel manually moving the arm stabilizer and/or the articulated arms. In some examples, the articulated arms may be placed in a clutched and/or unlocked state to allow manual movement of the joints of the articulated arm, and/or may be placed in a resistive state allowing the joints of the articulated arms to be moved, but with some resistance so as to avoid excessive movement of the articulated arms.

At an optional process 455, the one or more medical tools are initially placed. In some embodiments, once the computer-assisted medical device detects the attachment of an appropriate arm stabilizer (e.g., using the identifying features of the tool guide and/or by input from medical personnel), the articulated arms being held by the arm stabilizer may be placed in a special clutched mode. In some examples, when one of the articulated arms being held by the arm stabilizer is placed in a clutched mode by the medical personnel to place the medical tool located at the distal end of that articulated arm, that articulated arm may be manually moved by the medical personnel. To avoid placing undue strain on the arm stabilizer and the articulated arms, the articulated arm being held by the other end of the arm stabilizer may be placed in a following mode where one or more joint actuators of the articulated arm being held by the other end of the arm stabilizer are driven based on the kinematics of the arm stabilizer and the closed kinematic loop including the arm stabilizer and the two articulated arms being held by the arm stabilizer. In some examples, a position and/or orientation of a gantry of the computer-assisted medical device may be adjusted based on manual movement imposed by the medical personnel so that each of the articulated arms may be moving at the same time. In some examples, one or more forces and/or torques in the articulated arms being held by the arm stabilizer may also be monitored to reduce force and/or torque detected during process 455. In some examples, the various kinematic relationships and corresponding Jacobian transposes may be used to convert the observed forces and/or torques into position and/or orientation adjustments of the one or more joint actuators.

At a process 460, the one or more medical tools are placed. Based on the one or more medical tool poses determined during process 440, the corresponding medical tools are placed in their respective poses for the desired procedure.

In some embodiments, the one or more medical tools may be placed semi-automatically under the direction of medical personnel. In some examples, a special clutching mode, similar to the clutching mode used during process 455 may be used during the semi-automatic placement. To aid the medical personnel with the placement, the computer-assisted medical device may overlay one or more visual cues on images showing the computer-assisted medical device and/or the patient. In some examples, the one or more visual cues may depict a conical and/or other shape converging to the one or more desired poses for the medical tools. In some examples, the visual cues may include depiction of a virtual rendition of one or more of the medical tools and the corresponding pose for the medical tool. In some examples, haptic feedback may be used to direct the medical tool to the desired pose.

In some embodiments, the one or more medical tools may be placed automatically. In some examples, constrained trajectory planning between the two articulated arms may be used to automatically direct the one or more medical tools to the desired position and/or orientation. In some examples, the constrained trajectory planning may include planning a trajectory for one of the articulated arms being held by the arm stabilizer and placing the other articulated arm being held by the arm stabilizer in the special clutching mode described during process 455 using following and/or force and/or torque reduction. In some examples, the automatic placement may support a manual override control that allows medical personnel to abort the automatic placement.

At a process 465, a procedure is performed. Once the one or more medical tools have been placed during process 460, the one or more medical tools are ready for use. In some examples, constrained trajectory planning similar to the constrained trajectory planning used during process 460 may be used during the procedure to help coordinate the use and/or motion of the medical tools mounted to the distal ends of the articulated arms being held by the arm stabilizer. In some examples, haptic, visual, and/or audio feedback may be used to provide feedback to the medical personnel operating the medical tools so as to limit forces and torques on the articulated arms being held by the arm stabilizer. In some examples, the medical tools may be actively moved in synchronization with a physiological motion of the patient such as the physiological motions associated with respiration, heart beats, and/or the like. In some examples, images captured from an imaging device, such as imaging device 270, may be used to detect the physiological motion by noting changes in position and/or orientation of one or more markers associated with the patient. In some examples, the detected physiological motion may be used to detect changes in the patient to computer-assisted medical device kinematic relationship, which may be used as feedback to adjust one or more of the actuators in the articulated arms, end effectors, and/or medical tools to maintain a constant patient to computer-assisted medical device kinematic relationship.

In some embodiments, portions of the method 400 may be repeated as appropriate. In some examples, one or more of the processes 405-465 may be repeated to switch to different locations of the patient's anatomy, switch medical tools, switch tool guides, and/or the like.

As discussed above and further emphasized here, FIG. 4 is merely an example which should not unduly limit the scope of the claims. One of ordinary skill in the art would recognize many variations, alternatives, and modifications. According to some embodiments, additional control approaches may also be supported by the computer-assisted medical device while working with an arm stabilizer. In some examples, the computer-assisted medical device may monitor the patient table to allow for changes in position and/or orientation of the patient table. In some examples, the computer-assisted medical device may monitor the state of the table to medical device kinematic relationship (e.g., table to device-base kinematic relationship 365) and adjust the other kinematic relationships (e.g., the patient kinematic relationship 390) to automatically account for the movement of the patient table. In some examples, this monitoring may allow for automated adjustment of the tool guide without repeating processes 435-465).

In some embodiments, when the one or more medical tools used during the procedure of process 465 are used with cannulae, method 400 may be modified to include the use of the cannulae. In some examples, the cannulas may be docked to the patient (i.e., inserted through the body wall of the patient) before or after the arm stabilizer is attached during process 450. In some examples, process 445 of deploying the one or more articulated arms may include inserting the one or more medical devices in a respective cannula prior to the attachment of the arm stabilizer during process 450. In some examples, process 455 of initially placing the one or more articulated arms may include inserting the one or more medical devices in a respective cannula after the attachment of the arm stabilizer during process 450.

Some examples of control units, such as control unit 280 may include non-transient, tangible, machine-readable medium that include executable code that when run by one or more processors (e.g., processor 285) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted medical device, comprising:
   a first articulated arm;
   a second articulated arm;
   an arm stabilizer comprising first and second clamps and one or more sensors, the first and second clamps being configured to couple the arm stabilizer to the first and second articulated arms, wherein at least one of a distance or a relative orientation between the first and second clamps is adjustable and the one or more sensors are configured to determine the distance or relative orientation; and
   a control system configured to implement a following mode in which the control system drives movement of the second articulated arm in response to movements of the first articulated arm and the arm stabilizer.

2. The computer-assisted medical device of claim 1, wherein the first and second articulated arms each comprise one or more joint actuators and the control system is configured to drive movement of the second articulated arm by actuating the one or more joint actuators of the second articulated arm.

3. The computer-assisted medical device of claim 1, wherein the control system is configured to drive movement of the second articulated arm based on kinematics of at least one of the first articulated arm or second articulated arm.

4. The computer-assisted medical device of claim 3, wherein the control system is configured to drive movement of the second articulated arm further based on kinematics of the arm stabilizer.

5. The computer-assisted medical device of claim 1, wherein the control system is configured to implement the following mode when the first articulated arm is in a clutched mode.

6. The computer-assisted medical device of claim 5, wherein the movements of the first articulated arm are manually controlled when the first articulated arm is in the clutched mode.

7. The computer-assisted medical device of claim 1, wherein at least one of the first articulated arm or the second articulated arm comprises an end effector and the arm stabilizer is coupled to the end effector.

8. The computer-assisted medical device of claim 1, wherein at least one of the first articulated arm or the second articulated arm comprises a medical tool and the arm stabilizer is coupled to the medical tool.

9. The computer-assisted medical device of claim 1, wherein at least one of the first articulated arm or the second articulated arm comprises a cannula and the arm stabilizer is coupled to the cannula.

10. The computer-assisted medical device of claim 1, wherein at least one of the first articulated arm or the second articulated arm is coupled to the arm stabilizer by a link of the at least one of the first articulated arm or the second articulated arm.

11. The computer-assisted medical device of claim 1, wherein an angle of a central axis of a clamp of the arm stabilizer is adjustable relative to a spine of the arm stabilizer.

12. A method of controlling movement in a computer-assisted medical device, the method comprising:
positioning a first articulated arm and a second articulated arm of the computer-assisted medical device;
coupling an arm stabilizer to the first and second articulated arms;
adjusting at least one of a distance or a relative orientation between first and second clamps of the arm stabilizer, the first clamp coupling the arm stabilizer to the first articulated arm and the second clamp coupling the arm stabilizer to the second articulated arm;
determining the at least one of the distance or the relative orientation between the first and second clamps with one or more sensors of the arm stabilizer; and
implementing, with a control system, a following mode in which the control system drives movement of the second articulated arm in response to movements of the first articulated arm and the arm stabilizer.

13. The method of claim 12, wherein the first and second articulated arms each comprise one or more joint actuators and the control system is configured to drive movement of the second articulated arm by actuating the one or more joint actuators of the second articulated arm.

14. The method of claim 12, wherein the control system is configured to drive movement of the second articulated arm based on kinematics of at least one of the first articulated arm, the second articulated arm, or the arm stabilizer.

15. The method of claim 12, wherein the control system is configured to implement the following mode when the first articulated arm is in a clutched mode in which the movements of the first articulated arm are manually controlled.

16. The method of claim 12, wherein at least one of the first articulated arm or the second articulated arm comprises an end effector or a medical tool and the arm stabilizer is coupled to the end effector or medical tool.

17. The method of claim 12, wherein at least one of the first articulated arm or the second articulated arm comprises a cannula and the arm stabilizer is coupled to the cannula.

18. The method of claim 12, wherein at least one of the first articulated arm or the second articulated arm is coupled to the arm stabilizer by a link of the at least one of the first articulated arm or the second articulated arm.

19. The computer-assisted medical device of claim 1, wherein the arm stabilizer further comprises a memory device configured to store information associated with the arm stabilizer and wherein the control system is configured to read the information associated with the arm stabilizer from the memory device.

20. The computer-assisted medical device of claim 19, wherein the information associated with the arm stabilizer stored on the memory device comprises one or more of: an arm stabilizer type, an arm stabilizer identification number, an arm stabilizer model number, or arm stabilizer kinematic parameters.

* * * * *